US007797327B2

(12) United States Patent
Kataria et al.

(10) Patent No.: US 7,797,327 B2
(45) Date of Patent: *Sep. 14, 2010

(54) SYSTEMS AND METHODS FOR MANAGING THE DEVELOPMENT AND MANUFACTURING OF A BEVERAGE

(75) Inventors: Anjali R. Kataria, San Carlos, CA (US); Joseph Prang, Los Gatos, CA (US); Vinay Ambekar, Saratoga, CA (US)

(73) Assignee: Oracle International Corporation, Redwood Shores, CA (US)

( * ) Notice: Subject to any disclaimer, the term of this patent is extended or adjusted under 35 U.S.C. 154(b) by 344 days.

This patent is subject to a terminal disclaimer.

(21) Appl. No.: 11/859,725

(22) Filed: Sep. 21, 2007

(65) Prior Publication Data

US 2008/0133294 A1 Jun. 5, 2008

Related U.S. Application Data

(63) Continuation of application No. 11/022,316, filed on Dec. 23, 2004, now Pat. No. 7,275,070, which is a continuation-in-part of application No. 10/914,538, filed on Aug. 9, 2004, which is a continuation of application No. 10/052,412, filed on Jan. 23, 2002, now abandoned.

(60) Provisional application No. 60/263,177, filed on Jan. 23, 2001.

(51) Int. Cl.
G06F 7/00 (2006.01)
G06F 17/30 (2006.01)
(52) U.S. Cl. .................................... 707/756
(58) Field of Classification Search ........... 707/756
See application file for complete search history.

(56) References Cited

U.S. PATENT DOCUMENTS

| 5,664,112 | A | 9/1997 | Sturgeon et al. |
| 5,712,990 | A | 1/1998 | Henderson |
| 5,831,859 | A | 11/1998 | Medeiros et al. |
| 6,067,549 | A | 5/2000 | Smalley et al. |
| 6,243,615 | B1 | 6/2001 | Neway et al. |
| 6,256,640 | B1 | 7/2001 | Smalley et al. |
| 6,324,522 | B2 | 11/2001 | Peterson et al. |
| 6,397,115 | B1 | 5/2002 | Basden |
| 6,567,788 | B1 | 5/2003 | Johnson, Jr. |
| 2001/0049673 | A1 | 12/2001 | Dulong et al. |
| 2002/0188465 | A1 | 12/2002 | Gogolak et al. |
| 2003/0093295 | A1 | 5/2003 | Lilly et al. |
| 2004/0210473 | A1 | 10/2004 | Godard |

FOREIGN PATENT DOCUMENTS

WO  WO 2004/072868 A1  8/2004

OTHER PUBLICATIONS

PJB Publications Ltd. "A Tour of Pharmaprojects," Pharmaprojects Web/CD-Rom Version 5, PJB Publications Ltd. 2003, and referred to hereinafter as PJB.

*Primary Examiner*—Neveen Abel Jalil
*Assistant Examiner*—Michael J Hicks
(74) *Attorney, Agent, or Firm*—Townsend and Townsend and Crew LLP

(57) ABSTRACT

A system and method for managing the development and manufacturing process of a pharmaceutical is disclosed. The method comprises capturing and recording the development and manufacturing history of the pharmaceutical drug in order to generate a product history. The product history is stored on a computer and is searchable in multiple data dimensions in order to easily retrieve information. The system automatically provides compliance management procedures in order to comply with regulatory standards for the pharmaceutical industry.

35 Claims, 4 Drawing Sheets

SYSTEMS AND METHODS FOR MANAGING THE DEVELOPMENT AND MANUFACTURING OF A BEVERAGE

CROSS-REFERENCE TO RELATED APPLICATIONS

This application is a continuation application of U.S. patent application Ser. No. 11/022,316, filed on Dec. 23, 2004 now U.S. Pat. No. 7,275,070, which is a continuation-in-part of U.S. patent application Ser. No. 10/914,538 filed Aug. 9, 2004, which is a continuation of U.S. patent application Ser. No. 10/052,412, filed Jan. 23, 2002, now abandoned that claims the benefit of U.S. Provisional Application No. 60/263,177, filed Jan. 23, 2001, the entire contents of each of which are hereby incorporated by reference herein.

BACKGROUND OF THE INVENTION

1. Field of the Invention

This invention relates to management of regulated industries. In particular, the present invention facilitates regulatory, tax compliance, inventory and e-warehouse management of heavily regulated process industries.

2. Description of the Related Art

Heavily regulated and process oriented industries such as: Oil & Gas, Food (e.g., agriculture products, processed food, meat/poultry etc.), Beverages (e.g., consumable liquids such as spirits, wine, beer, juice, etc. . . . ), Chemicals, Consumer products (e.g., cosmetics and skin care), and Pharmaceutical Drugs {e.g., Chemical Development (also known as Drug Substance), Pharmaceutical Development (also known as Drug Product), Biopharmaceuticals (Drug Substance and Drug Product) as well as Generics} share a number of common characteristics. These kind of heavily regulated process industries are highly regulated by local, state, federal and international agencies (i.e., Food and Drug Administration (FDA), Trade and Tax Bureau (TTB part of Treasury) to ensure that safe and efficacious products are consumed by the public and that each of the products presented by companies in these aforementioned industries are not fraudulent or harmful (i.e., that the product integrity is maintained for the life of the product). The product integrity is proven by comparing product records at one point in time against product history records of another point in time during the development, manufacturing and commercial sale of these products. This is challenging for these kinds of heavily regulated process industries because by nature they tend to produce products that are dynamically changing or very complex. Thus the information associated with these product history records becomes more difficult to manage. For example, these industries may require highly variable raw materials such as proteins secreted form mammalian cells or grape juice secreted from agriculture vine-grapes.

Another major requirement for "heavily regulated industries" is the ability of a company to demonstrate that it's production processes from development through commercial manufacturing are fully traceable, meaning that a third party (such as an Agency i.e. FDA) could come in and demand to see product history from one point in time to another. For instance, a company must be able to prove that "what it is producing is indeed being produced, in the manner it claims to be being produced in." These onsite inspections, audits, and information requests often focus on a particular process for a particular set of materials from one point in time to another. Failure to provide immutable proof of product history traceability has subjected companies to hefty fines as well as shutdowns.

In addition for failure to provide proof of the process over time, these industries are usually subject to large fines or delays in production/shutdowns for non-compliance of any part of the submission application, audits, labels, waste, emissions, safety, etc. Payment of appropriate taxes is an ongoing challenge as the payments are determined by the "amount produced" and "type" of product produced, all of which require extensive record keeping along many dimensions over time.

These industries are also "heavily process oriented" meaning that products are produced in a manner that consists of extensive combinations of steps such as complex blends, formulations and recipes. Another drawback is that in some of these industries (e.g., the pharmaceutical and beverage industries) extensive record keeping is required to create the product history "paper trail". Typically, the kind of record keeping required by these industries is a complete history of the product's lifecycle, often spanning from the raw materials to the final product and inclusive of all intermediate products across the supply chain. The type of information required in the record keeping of product history typically spans the following dimensions: personnel and their training requirements, process, materials, equipment, standards, and facility/environment information which collectively form the comprehensive information for the specified record.

These industries may also have complex order tracking for work personnel, equipment materials, processes (e.g., campaign planning and execution, work order generation, etc.). For instance, tracking the state of materials from raw material to intermediates, to final products etc. or tracking the equipment history (calibration, cleaning, usage, etc.) requires a number of different kinds/pieces of information making it a complex process. Not only does the information in these areas have to be recorded and tracked, but it must be compared to standards set both internally within a company and externally by regulating authorities. Furthermore, it must be compared to itself at differing points in time (e.g., Commercial Manufacturing takes place in Year 9 and the equipment set up, calibration, cleaning, usage must be recorded, tracked and compared against the equipment history in Year 8, which was submitted to the FDA and is what the company's license to commercially manufacture is based upon.)

These types of regulated process industries are further challenged in that a number of different indirect/input goods are produced along the path of creating the final product and all of these indirect/input/intermediate goods have be managed in a similar manner of recording information/tracking/comparing to different points in time as described above. Visibility is essential to achieving this comprehensive record keeping and management of information in these regulated process industries, yet at present these industries have low visibility at all levels of process input and product history across the supply chain.

Currently there are no broad web-based solutions that fully meet these kinds of complex needs such as comprehensive product history record keeping in process management of heavily regulated industries. In fact, many of the record keeping functions and filing processes for federal and state regulations still occur through outdated manual time-consuming means.

SUMMARY OF THE INVENTION

The present invention describes a system and a method for enabling information management across the supply chain from raw material to final product for regulated process industries. The system and method enables a company to manage extensive record keeping for heavily regulated products where the key components are often dynamically changing and are very complex to manage. The embodiments facilitate regulatory and tax database with automated compliance and tax reporting. For example, regulatory management and automated compliance are achieved by the system enabling a company to automatically demonstrate compliance with federal regulatory agency submission requirements (i.e., FDA Development History, Chemistry Manufacturing and Controls (CMC) and Pharmaceutical Development (Drug Product) submission requirements for license to manufacture drugs in the U.S.); traceability of any dimension of drug development, and retrieval of key information necessary to meet audits, inspections, and product integrity inquisitions. Because the system and method is integrated with smart inventory and e-warehouse management solutions, the essential product history information from "candidate selection to commercial manufacturing" is automatically captured for comparisons, correlations, and verifications enabling the company to demonstrate compliance to the federal agency. For example, the full lifecycle management of raw materials, expendables and intermediates can be demonstrated. This information associated with raw materials and intermediates at each stage is cleverly and smartly leveraged into the record keeping needs of the company to demonstrate full product history of the lifecycle. The embodiments are applicable to heavily regulated industries such as, for example, beverages, food, oil, pharmaceutical drugs, and chemicals.

The present invention allows regulatory compliance integration with complete, real time web-based supply chain infrastructure to manage all essential product history from raw material stage to final product. The system has enough customization for each industry allowing the domain, regulatory and tax specificities to be appropriately addressed. Complete Product history includes key information along the essential dimensions of product development and manufacturing: People, Process, Materials, Equipment, Environment/Facility and Standards (regulatory and internal). The present invention allows for management of regulatory (standards) with automated compliance, tax reporting and in-process inventory management of development and production of pharmaceuticals.

The present invention provides industry-specific solutions to regulatory and tax compliance issues, including integrated industry-specific supply chain applications to assist in compliance. The present invention is designed to operate alongside existing information systems (such as ERP, MES, LIMS EDMS, etc.) to provide complimentary applications.

The system enables users to manage regulatory filings (such as the IND, NDA, BLA and ANDA), tax compliance, and inventory (raw material, excipients, additives, intermediates, final products both quarantined and released). This aspect reduces supply chain inefficiencies with a real-time, web-based, enterprise-wide supply chain infrastructure. A substantial reduction of the current cumbersome paper trail is achieved by the system and affords users a more accurate and timely compliance, thus avoiding violations and substantial fines/penalties.

The system may provide supply chain solutions to increase visibility throughout a regulated industry's operations. This aspect enables greater information management through secure access to real time information; and advanced planning. This aspect provides users worry-free management while reducing costs, inventory levels, and decreasing working capital needs. The system can be wireless ready, enabling the user to more efficiently and effectively manage critical data.

The system may provide clear comprehensive product history information, enabling the company to demonstrate product integrity and to show product traceability from one point in time to another along multiple dimensions of: people, process, materials, equipment, standards and environment/facility.

Through an extremely scalable platform, the system can enable real time web-based regulatory and tax compliance based supply chain infrastructure while also providing regulatory and tax compliance, inventory management, content management and supplier catalog management modules. Procurement, shipping management, demand and forecasting tools and regulatory e-filings complement the supply chain solutions.

The system can interface with many third party enterprise resource, planning applications and existing legacy systems. The system can be java-based, using open API systems, and can be highly scalable, flexible, robust, modular and portable (PDA and wireless capable). The system can use thin client architecture requiring only a web browser and implemented without requiring desktop installation. The system can support Secure Sockets Layer (SSL) to protect the transmission of content between the browser and the server. In addition, user identification and password protections may be embedded, as well as controls based upon user roles.

The system of the present invention through the use of a core platform and modules can provide extensive management of record keeping across multiple dimensions over time. For instance, material management functionality for the pharmaceutical manufacturing industry is provided by the system and method. Specifically, the chain of custody for drug substances can be recorded such as the starting materials, reagents, solvents, intermediates, bulk and final API. The system manages all related information for each material type (COA's, Specs, etc. . . . ). Material traceability from loading dock to "tablet" is provided by knowing with certainty the who, what, where, when and how of all materials. Furthermore, it is possible to create and locate materials. Requests, orders, inventory, dispense, dispose and transfer of materials are known. The chain of documentation is also recorded through the use of status, signoff, alerts, authentication, e-signatures, and hazard profiles. Similar functionality exists for all dimensions of pharmaceutical development over time (as mentioned above and further explained below).

The quality of the product can be managed by the system. The material qualification ID and use tests are recorded, as well as raw material specifications. Materials can be sorted and tracked on any characteristic of the material by the system (ex. evaluation date, purity).

The system can also manage the equipment used in the manufacturing process. Reservation for equipment use, as well as equipment characteristics, usage and availability can be viewed with the system. Furthermore, equipment usage, loaning borrowing, and decommission can be tracked. The maintenance and cleaning of equipment can also be tracked with the system.

Those skilled in the art will appreciate these and other advantages and benefits of various embodiments of the invention upon reading the following detailed description of a preferred embodiment with reference to the below-listed drawings.

DETAILED DESCRIPTION OF A PREFERRED EMBODIMENT

Figure 1:
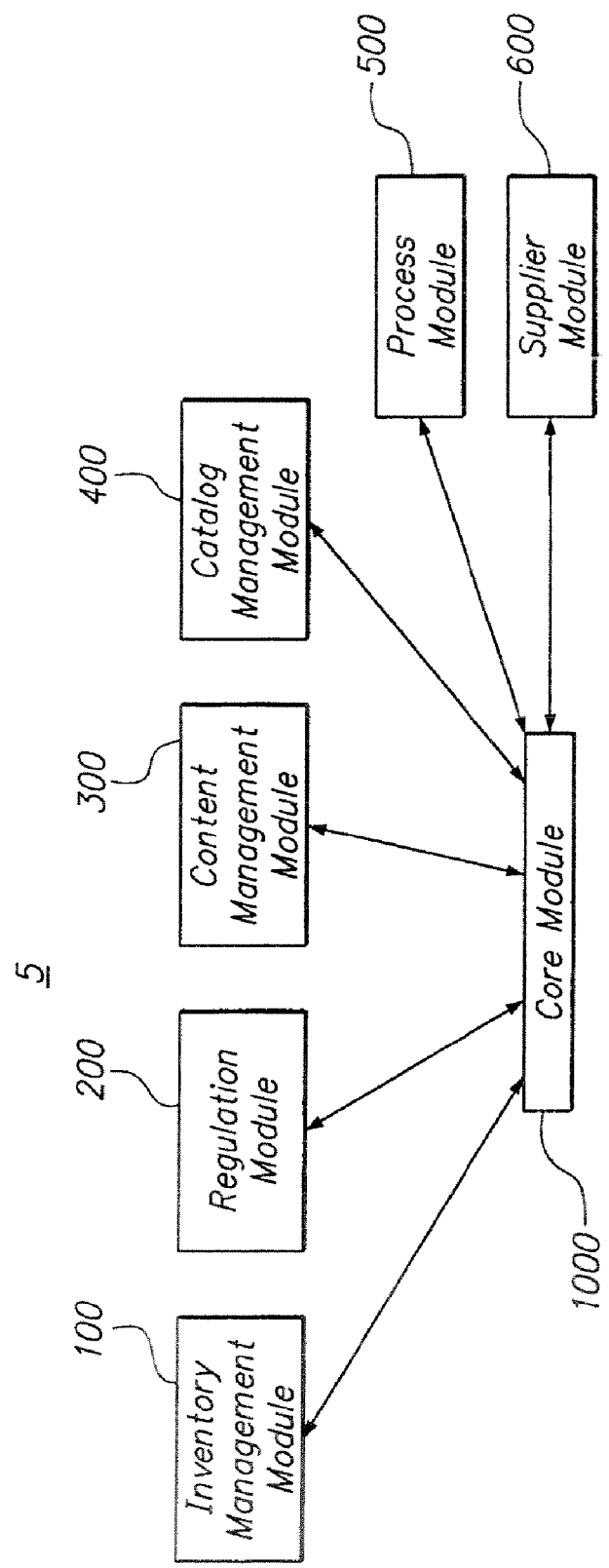
FIG. 1 is a block diagram of a system according to a first embodiment.

FIG. 1 is a block diagram of a product conformance management system 5 having an inventory management module 100, a regulation module 200, a content management module 300, a catalog management module 400, a process module 500, a supplier module 600, and a core module 1000. It will be recognized by those of ordinary skill in the art that the number and types of modules available may change on the type of industry. For example, for the pharmaceutical industry, there may also be a material management module, an equipment management module, a standards module, a method execution module, and a traceability module. In this regard, a solution for a specific industry may contain many suites which are a collection of modules. Each of the modules is independently deployable on the platform. By having the multiple modules, the solution can be easily deployed and expanded at customer sites in a phased manner.

The inventory management module 100 includes domain knowledge of the pharmaceutical industry to specifically address the needs of that industry. Specifically, the inventory management module records the movement of raw and starting materials as they move through the production process. In addition, the inventory management module 100 provides visibility into a company's inventory of material (raw, intermediate, bulk and final product) at any location at the subsidiary or corporate level, as well as tracks the inventory through the production process. The inventory management module 100 implements inventory threshold levels for reorder points and compliance requirements and triggers a notification via the system, email, pager or WAP. The inventory management module 100 also provides the ability for both the manufacturer and their supplier to view internal inventory levels. The inventory management module 100 provides for receipt, issue and return of goods, movement of goods, and verification of goods locations. Accordingly, the inventory management module can track goods through the development process into and through the production cycle.

The regulation module 200 addresses the need for compliance with complex and varied federal and state regulations for pharmaceutical production. The regulation module 200 provides current regulatory and tax compliance information affecting the pharmaceutical industry. This regulatory and tax database will also include automated compliance and tax reporting. The regulation module 200 will be linked with the Federal Drug Administration (FDA), state agencies, and other on-line sources of legal information to create this database. The key components of the regulation module 200 are centered around the submission process of investigational and new drug applications for chemical, biological and generic entities. The module 200 combined with the platform (core module 1000) enables an electronic product history record (ePHR) to be created for both development and manufacturing. At present, this product history record can be specific in the Pharmaceutical Industry to the Development environment (called an electronic development record (eDR)) or to commercial manufacturing (called an electronic Product History Record (ePHR)).

The ePHR and eDR are both created automatically from the extensive record keeping functions in the system which have key pieces of information relating to the various dimensions of development over time. The dimensions of development include: people, process, materials, equipment, standards, environment/facility. The ePHR and eDR provide context around the chemical or biological structure enabling downstream and upstream development and manufacturing colleagues to capture learnings and compare product histories between different compounds, stages, conditions, etc. . . . Once a new chemical or biological structure is identified ("candidate selection") the system 5 captures key information along the various dimensions automatically creating the eDR and ePHR.

The ePHR and eDR enable companies to meet pre-approval inspections and post approval inspections conducted by federal agencies more effectively; to gain approvals for drug applications more readily; and to produce products at a higher level of quality, with greater visibility, and in a more efficient manner. Furthermore, the eDR and ePHR enable companies to demonstrate appropriate and necessary information to pass onsite and remote audits and to provide faster and more efficient means for submitting post approval changes. The ePHR and eDR also provide faster and better resolution of "out of specification incidence" (OOS) in both Development and Manufacturing of Pharmaceutical Drugs. Ultimately, over time, companies can expect a greater level of "process understanding" as the ePHR and eDR enable complex information to be aggregated in one place with context and dimensions of development preserved over time and over the life of the product. Any authorized user has the ability to search, retrieve, analyze and correlate any component of the ePHR and/or eDR to facilitate greater process understanding.

The content management module 300 is a relational database of industry-specific, company-specific, activity specific or supplier-specific information such as documents, inventory alerts, specification sheets, Certificates of Analysis (COA), Methods, Standards (both company specific or internal as well as external/Agency specific).

Suppliers that sell products typically have some sort of catalog, whether it be online or in hardcopy. The catalog management module 400 provides the manufacturer with a consolidated view of similar products across a number of suppliers and provides the company with a list of ingredients, cost associated with each product, procurement related information to each product and quarantine/release information.

The process module 500 captures data from various stages of the pharmaceutical production. The captured data can include activity records or lab analyses records. The records allow traceability for audit and regulatory compliance of all stages of material (from raw material to intermediates to bulk product to final product). Process module 500 also enables extensive record keeping through campaign planning and execution, tying all process steps, people involved, equipment used, materials used/stage, standards followed, lab condition and facility location information. The culmination of this process information enables the physical and chemical attributes of the new "heavily regulated" compound being developed to be managed more efficiently. By linking the chemical or biological structure to the process steps in the aforementioned manner, the system 5 is able to more effectively manage the regulated process industry (such as pharmaceuticals). Moreover, the same methods applied to chemical entities are also applicable to biopharmaceutical entities and generic products.

The supplier module 600 provides the company/user the ability to manage suppliers and the associated catalog of products purchased by the company as well as the costs associated with the transaction. For example procurement of raw materials, excipients, or starting materials in the Pharmaceutical industry occurs at multiple stages over time. Material procurement needs change, as the product being developed progresses from Candidate Selection to Commercial Manufacturing (e.g., purity levels of required starting materials at Candidate Selection time period are much higher than starting materials used in Commercial manufacturing time periods). Hence, the information associated with each and every starting material must be captured along the way or "in process" and this information is typically provided by the supplier in the form of a "Certificate of Analysis". Because these kinds of information/record keeping must be comparable from one time period to another, companies must record and track this information. Currently tracking is done by manual or hand processes and is very cumbersome. Supplier module 600 along with core module 1000 enables the company to have an automated system for tracking and recording this type of information.

The core module 1000 (also referred to as the "Product Conformance Management (PCM) Platform) is the base module for the system 5. The core module 1000 implements the functionalities of the system 5 and is a common platform that can be configured by the customer for various business and regulatory processes in the company. The core module 1000 manages the library of all information regarding material, equipment, process, people, standards and environment related to a customer's regulated process. The core module 1000 dynamically defines all attributes according to the customer's requirements. The core module 1000 provides valid values (either ranges or enumerations) and defines data types and value generation algorithms (if any). The core module 1000 can also define units of measure and support conversion between different units.

Furthermore, the core module 1000 manages the states of all information objects, workflow for approval and "state" changes (i.e., management of the dynamic and highly variable changes). Sites and locations, as well as organizational hierarchy is managed by the core module 1000. The core module 1000 manages users, user groups and user functions and provides the infrastructure for setting up alerts and delivering notifications to the users subscribed to the alerts. The core module 1000 moves data between software systems in a validated mode and ensures compliance with government regulations (e.g., 21 C.F.R. Part 11). Furthermore, versioning support is provided in the core module 1000. The core module 1000 also creates an audit trail of changes to the data captured in the system, attachments to any information object in the system and any number of notes attached to any information object in the system.

In order to maintain the security of the system 5, the core module 1000 provides access through a login which is a combination of user identification and a password. After three unsuccessful attempts, the user account should be disabled and an administrator notified. Only an administrator should have the ability to unlock the account. Additionally, details about the user name, title, email address, telephone number, effective dates of usage of the system and the physical location of the user are maintained by the core module 1000. The login service also identifies any of the applications of the system 5 that are authorized for the user to access and the role in which the access is permitted.

The core module 1000 also provides external authentication support by which users can be authenticated by an external system. The externals service is called with the user's identification and password. The core module 1000 can handle successful and unsuccessful attempts similar to the authentication process within the system 5. When external authentication is used, all account and password management should be handled by the external service.

The system 5 can model various roles for access. These roles would not have to map to functional roles of the individual within the enterprise. The roles defined in the system are primarily used to control the access to various features of the system. Roles can be associated with an application or made available to all or a combination of applications. Roles may be location specific or enterprise wide. A user has the ability to have more than one role in the system. The role identifies the functionality of the system the role can access (e.g., menu items, screens, etc. . . . ). Furthermore, the role identifies actions the role can execute on the functionality it can access (e.g., read, write, update, delete, list, etc. . . . ). The role identifies the specific fields/attributes that are accessible.

In order to authenticate the input of records into the system 5, the core module 1000 supports the use of a generic method of collecting user signatures electronically. This service will be invoked by the applications when ever the requirement for an electronic signature arises. The user will be prompted for the user's ID and password which will be verified for accuracy. A reusable user interface component is available for all applications to ensure easy and consistent implementation of electronic signatures. This reusable component accepts the user's ID as a parameter and pre-fills that information when the user interface is presented to the user. This is an aid when a continuous set of signatures is needed to be accepted. Each signature is stored against the activity or information being certified/signed off by the user.

Alerts are very important to the system 5. Alerts will be used for a large number of activities and pro-active notifications. Therefore, the alerts are highly scalable and generic. Customers can associate alerts to objects identified by an application at any time without having to shutdown the system.

Each application identifies objects that are expected to have alerts associated with them (e.g., work orders, material receipt, equipment schedule, etc.) and the various attributes of the object whose change of value would result in an alert. It is possible to define the type of comparison that is performed against the attribute to generate the alert. All common types of comparison—equality, inequality, greater than, lesser than, range or list, can be supported.

Types of actions which trigger alerts are user actions which change an object (create, modify, delete) and time based triggers (check overdue activities). Optionally, it is possible to attach a custom code to be executed when the alert condition is reached. This will help embed computational logic, if required for generating notifications.

In a deployed system, an administrator is able to publish the alerts that are available to the users of the system 5. This is done by identifying the roles and/or users who are allowed to subscribe to a given alert. Publication is achieved through the generic system wide publish/subscribe mechanism When a user attempts to subscribe to alerts, only those published to the user and the user's role should be listed. Users can then choose the actual alert that they want to subscribe to and provide the information required to complete the subscription. Through a user interface, the end user is able to define the exact conditions when they want to be notified. The end user has the ability to select the object and its attributes and assign the values which would trigger the notification. Depending on the user's object level permissions, the user can specify notification criteria only for attributes the user has read access.

The user has the ability to select the method of delivery of the notification. Notifications are delivered to the user's personal alert list in the system 5. Additionally, the user can choose to have the alert delivered by email. It will also be recognized that alert notifications can be delivered to pagers and cell phones.

Ensuring that the user is properly alerted is a key responsibility of the system 5 and hence the core module 1000. An alerts pane on each of the pages of the system 5 is generated by the core module 1000. The pane identifies the alert and some key attributes of the notification. When the user is active in any application of the system 5, the alerts pane is constantly updated with the latest notifications that have not been acknowledged by the user.

All notifications to the user are viewable through an interface dedicated to alert notifications. The user is able to view all of the relevant details of the notification through this interface and also manage the notifications. The user is able to acknowledge having seen the notification so that it is no longer shown in the alerts pane and/or delete the notification.

Applications of the system 5 need to co-exist with multiple commercial enterprise applications and niche products, as well as with many custom in-house solutions. For successful deployments of the applications and to achieve being a repository of electronic product development, the core module 1000 should be capable of easily exchanging data with other systems. To achieve this, the core module 1000 provides an integration framework that is used to configure or build the integrations. The framework complies with the following requirements:

Middleware Independence

No assumptions should be made based on vendor specific middleware products. Deployment engineers should be able to configure the framework to communicate with any external system or middleware (e.g., TIBCO, WebMethods, SeeBeyond, Vitria, etc.) which may be specified by the customer. Only industry standards like web services and JMS should be supported.

XML Data Format

Data moving between the systems should be encoded in XML to conform to industry trends. Existing industry standard specifications like BatchML from World Batch Forum can be supported.

Integration Event Based Triggers

The framework can move data in real time, based on data modification triggers as well as through periodic batch mode updates.

The integration framework can hook into the generic system wide alert notification framework to achieve this.

Back-End (Application Level) Integration Support

Based on event triggers, the framework should be able to post the data to a web service, URL (http port), JMS server, or through simple export to sequentially labeled files. The integration framework should be able to accept incoming data through a web service or a JMS server.

Bi-Directional Data Exchange

The system 5 can publish data out from the system as well as ability to insert and modify data within the system.

Identification of System of Record

The system 5 has the ability to define a list of applications and identify one of the systems as the owner of record (master) for each data item.

Organizational Mapping

Generally the name of the organizational unit will be required to provide the context of the data being exchanged. The name given to a particular organization unit may differ between different external systems and between those of the system 5. The core module 1000 provides a means of mapping these names. This mapping should not be assumed to be a simple 1<->1 mapping.

Attribute Mapping

One data item may be identified by two different names in two different systems. The framework should provide a generic name mapping functionality (for example where integrations are deployed without middleware). Mappings should be configurable on-site both during and after deployment. It should be possible to associate multiple groups of mappings with a particular external system, using mapping set identifier(s).

UOM Mapping

For parametric data it is common that the unit of measure used in the source system for a particular data item is different than the unit of measure that the target system is expecting. The integration framework should include a mechanism to handle this. The mapping should be configurable on-site both during and after deployment. It should be possible to associate multiple groups of mappings with a particular external system using mapping set identifier(s).

Backward Compatibility

The framework defines a published open API. Minor revision version changes to the API should not require changes to integrations built using the API. Where there is a version incompatibility, the version mismatch should be detected and reported.

Performance and Scalability

Transactions need to be processed in direct proportion to the number of transactions processed by the system 5. Theoretically, an edit of any object in the system could trigger a data movement through the integration framework. The end-to-end delay and throughput overhead imposed on transactions by the integration framework should not be a major factor in the overall end-to-end delay or throughput experienced by the actual user.

Logging

Data exchange events are logged with errors for debug by the framework. Optionally, debug logs are available to help track data movement. All logs are at user specified locations and should be self-maintaining. When a log reaches a preset size it should be closed and renamed as an archive with logging continuing to an new file.

Administration Support

The framework provides a user interface for the administrator to identify all active configured integrations (e.g., objects for which messages are being published or received)

and monitor their health. The administrator can configure new integrations, enable and disable specific integrations, and inspect (debug, event, error) logs from this interface.

System Configurability

Data to be exchanged, data mapping and direction of the exchange are configurable at the time of deployment based on the needs of the customer. Configuration can be limited to certain entries in configuration files and some graphical user interface driven data entry.

A goal of the system 5 is to enable information sharing. Though a database based system makes this easy to achieve, there are many instances where different pieces of information have to be specifically delivered to a user or an external interface. To achieve this, the system 5 provides a generic mechanism to publish and subscribe information. The mechanism has the ability to register various objects in the application that may be a candidate for publication. The objects may be alerts, score cards, reports, data packages, etc. The rules for publishing are based on the type of object being published. The system can support three types of publication:

System Defined—Pre-configured in the system and cannot be removed;

Administrator Defined—managed only by the administrator; and

End User Defined—managed by the end user.

At the time of publication, it should be possible to identify the users, user groups and roles that are authorized to subscribe to the publication. All users in the system can look up the various alerts that have been published to them and decide which ones they want to subscribe to. It may be possible for the user to provide additional information to identify objects of their interest while subscribing to a publication. For example, while subscribing to an alert, the user can provide the condition under which a notification should be generated.

Workflow is an important and critical service provided by the system 5. In any business, processes, roles and functions change constantly. It is possible to associate states and routing information to any object in the system and use the work flow mechanism to ensure that the object gets routed accordingly. The system 5 is able to support a default workflow for an object as well as an operating mode specific workflow.

The application programmer can register objects types in the application that would go through a workflow. The application can trigger a workflow based on its internal logic. The workflow service determines the current state of the object and propagates it through the workflow based on the state. The state sequence is defined and controlled by the user in the transaction layer of the system 5.

Workflow enables routing serially from one user to the next or parallel to multiple users from one user. Furthermore, workflow enables synchronization after parallel routing or routing to a user or user role. Optional recipients of the object whose actions will not alter the state of the object are also routed. Workflow also enables routing to backup approvers if no response is received from the primary approver within a user defined time limit. End users should be able to see the workflow an object goes through and also the current position of the object in the workflow.

Whenever an application submits an object for routing, the workflow manager determines the current state and generates an alert for the next user/users in the chain. The user can get to the actual object directly from a hyperlink on the alert notification, by locating the object from its corresponding 'Locate' page or from the list of pending activities in user's home page or workspace.

Once the user gets the object, the user is presented the list of actions that the user can take on the object. These actions will be determined by the state transition sequence defined for the object.

Many industries are highly document driven. Quite often certain pieces of information of interest to users are available only in a document. It is also difficult to predict which objects in the system will have attachments. This requires a generic framework through which a user can attach a document to any object in the system that the user has permission to create. Users should be able to identify the file on the local system which is to be uploaded to a controlled shared area on the server. All users with permission to view the primary object would also be allowed to view the attachment. There should be no limit on the number of attachments that an object may have. The local system can have the viewer capable of displaying the attachment.

An application programmer should be able to register object types for life cycle management. This registration should ensure that all objects of that type are committed to an audit trail. In future releases of the platform, it should be possible to reconstruct the object through the user interface. It should be possible to determine at one place in the system all the object types that are being collected in an audit trail.

Each and every object in the system 5 has a date and time stamp. The time stamp is accurate to the nearest second. Irrespective of the physical location of the user, the stamps should be in a single time zone for all objects in the system. There should not be any ambiguity about the sequence of events.

The data model layer of the core module 1000 provides extreme flexibility to the developers of applications for the system 5 and to end users who need to define key objects in the system. The data model layer provides the framework for building various dimensions of the system that need extensibility even after deployment. The system 5 provides the ability to define new object sets and build a classification hierarchy under them. Application programmers may use the generic access functionality to manipulate the objects or define their own specific objects to implement specialized business logic. Reusable user interface components are available to invoke the functionality provided in this layer within applications.

It is possible to add a new object category at any place in the hierarchy. Adding a new category would require the user to identify its location in the hierarchy and give it a unique identification. A category's name should be unique within its hierarchy.

Once a category has been added to the hierarchy, it is possible to define the properties of the category. This would require the user to provide the name for the property, the data type and size, identify whether the value in the property should be unique, define default values for the property, and define valid enumerated values or value ranges. Typically, a category should inherit the properties of its ancestors.

Though having information about objects in each dimension in the system is helpful, being able to create relationships between dimensions is a critical requirement. The system 5 is the repository for electronic development records and tracking relationships between the various dimensions is a major focus. Application programmers can register relationships between objects and the properties of the relationship. This concept can be extended to ensure that additional relationships can be created as a part of the deployment task.

The behavior of core module 1000 and the applications built on it is dependent on the operating modes configured on the system. The operating mode is a key factor determining the workflow associated with any object, the states an object passes through, and rules for verification of the data. The core module 1000 defines any number of operating modes for the system 5. Applications will use the operating mode to determine their behavior.

Default and valid values for attributes may be defined in the data model layer for the various dimensions. However, these values are subject to change based on operating modes. Additionally, the verification of data pertaining to the transactions themselves should be dependent on the operating mode. This requires the platform to provide a service for defining the verification criteria dependent of the operating mode. If such criteria is not provided at this layer, the system should default to the criteria provided in the data model layer.

For any object that needs to go through a workflow, it is possible to define state transition sequences. State sequences may vary by operating mode and/or location and it is possible to alter the state sequence. When such changes occur, the state sequence should be versioned so that it is possible to determine the exact state sequence an object passed through.

It is hard to predict all the reports required and computations that need to be done on large data sets like electronic development records. The core module 1000 has 'Locate' functions in the system 5 to provide various easy methods of getting to this complex data. Since Excel is the tool of choice for many industries, users have the ability to export the data returned from these searches to Excel.

Each application within the system 5 should be able to define its reports and associate them with a role. These reports are available to all the users assigned to the role. The reports may typically be defined using an external report writer and may be served by the corresponding report generator. Need for new reports rise regularly at most companies. So, it should be possible to continuously add new reports to the system and associate them with the roles defined in the system. This should ensure that the user's choice of reports is automatically updated when the user logs into the system.

User should be able to provide search criteria for the report being requested. This will ensure that the user gets a report only for the subset they are interested in. Applications of the system 5 can pre-define data packages of interest to the application. These packages may be a collection of predefined reports and can include score cards, checklists and search criteria within the system. Once the package is defined, it should be possible to publish it and subscribe to it using the generic publish/subscribe service of the platform.

The core module 1000 provides a generic framework for defining dashboards. These dashboards should provide aggregate visibility based on a type of object in the system. Primary objects in the dashboard would be objects such as fixed equipment at a location, currently active tickets at a location, currently active projects at a location, material staging requests at a location, various steps of a particular campaign, etc.

The user should be able to drill down into the details of any of the individual objects from the dashboard. The dashboard displays links to other related objects so that the user can also look up related information. Usability and information aggregation should be such that the dashboard should be one of the most common points of access for any application.

Applications of the system 5 will be used in large corporations which have world wide operations. This automatically translates into requirements to support the variations that you come across due to local standards. The core module 1000 and applications of the system 5 should be internationalized and should be able to support user definable date format (dd/mm/yyyy, mm/dd/yyyy and dd-mon-yyyy), user definable time format and time zone, user definable 1000s separator and radix point, and user definable units of measure. Because the system is highly configurable, all configuration information which will be part of the 'perceived' static part of the user interface should also be localizable.

Figure 4:
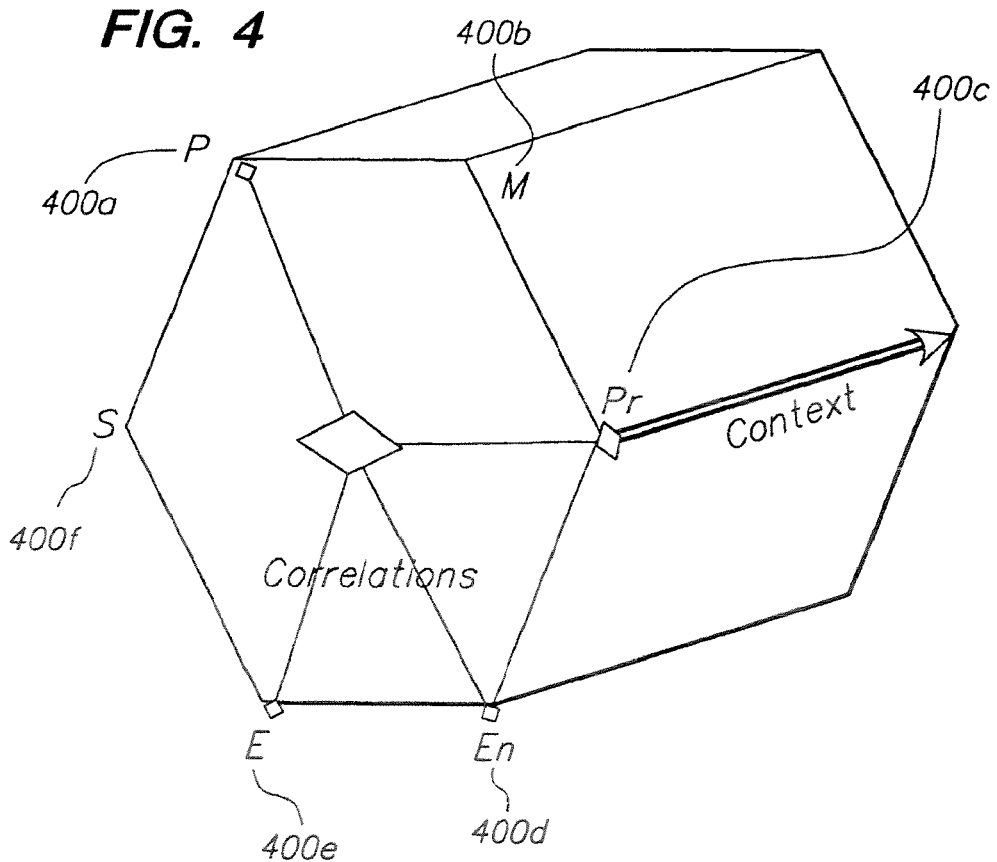
FIG. 4 illustrates the dimensions of data to be collected and analyzed.

The information collected by the core module 1000 and related applications and modules is stored and sorted in a data model layer that enables correlations between information to be sorted. Specifically, the data is stored among multiple dimensions that represent all key development activities. Referring to FIG. 4, the dimensions 400 are people 400a, materials 400b, process 400c, environment/facilities 400d, equipment 400e and standards 400f. It will be recognized by those of ordinary skill in the art, that the dimensions may consist of different labels if desired. Each dimension classifies the type, attribute and status of the information that is recorded with the system 5. For example, the equipment dimension 400e and material dimension 400b classifies the type, as well as defines the attributes and hierarchy of the equipment and material. Furthermore, both the equipment dimension 400e and the material dimension 400b sets default limits and valid values for the equipment and material. The people dimension 400a classifies the roles and groups of people as well as defines the roles hierarchy and privilege access. The people dimension 400a also sets default limits and valid values. The process dimension 400c classifies the type of processes and defines their hierarchy. Furthermore, the process dimension 400c sets workflow and business rules and creates workflow templates. The environment dimension 400d classifies the type of environment, as well as define the attributes and hierarchy thereof. This also refers to the actual facility the processes are occurring in. Default limits and values are set in the environment dimension 400d, as well as environmental reference standards. The standards dimension 400f can classify the type of standards and create structure data standards. Furthermore, the standards dimension can categorize reference documents and pre-defined processes.

Correlations can be made between the different dimensions in order to sift through the data. For example, uses of correlations include searches for related information, comparisons, verifications, review status, context, etc. . . . . The correlations can be used over time and events in order to determine the "context" of the information. For example, referring to FIG. 4, the people, process, environment and equipment dimensions 400 are correlated in order to give context to the information. The information can be located at any time for a given event (i.e., condition). The context, correlation and dimension data structure allows the electronic development record (eDR) of the material to be easily searched. In this respect, the electronic development record provides alerts and notifications, in-process operational management, knowledge management and development history archival.

Over time, the eDR enables companies to correlate process understanding to particular steps in the process, materials, and structure of chemical and biological entities.

Figure 5:
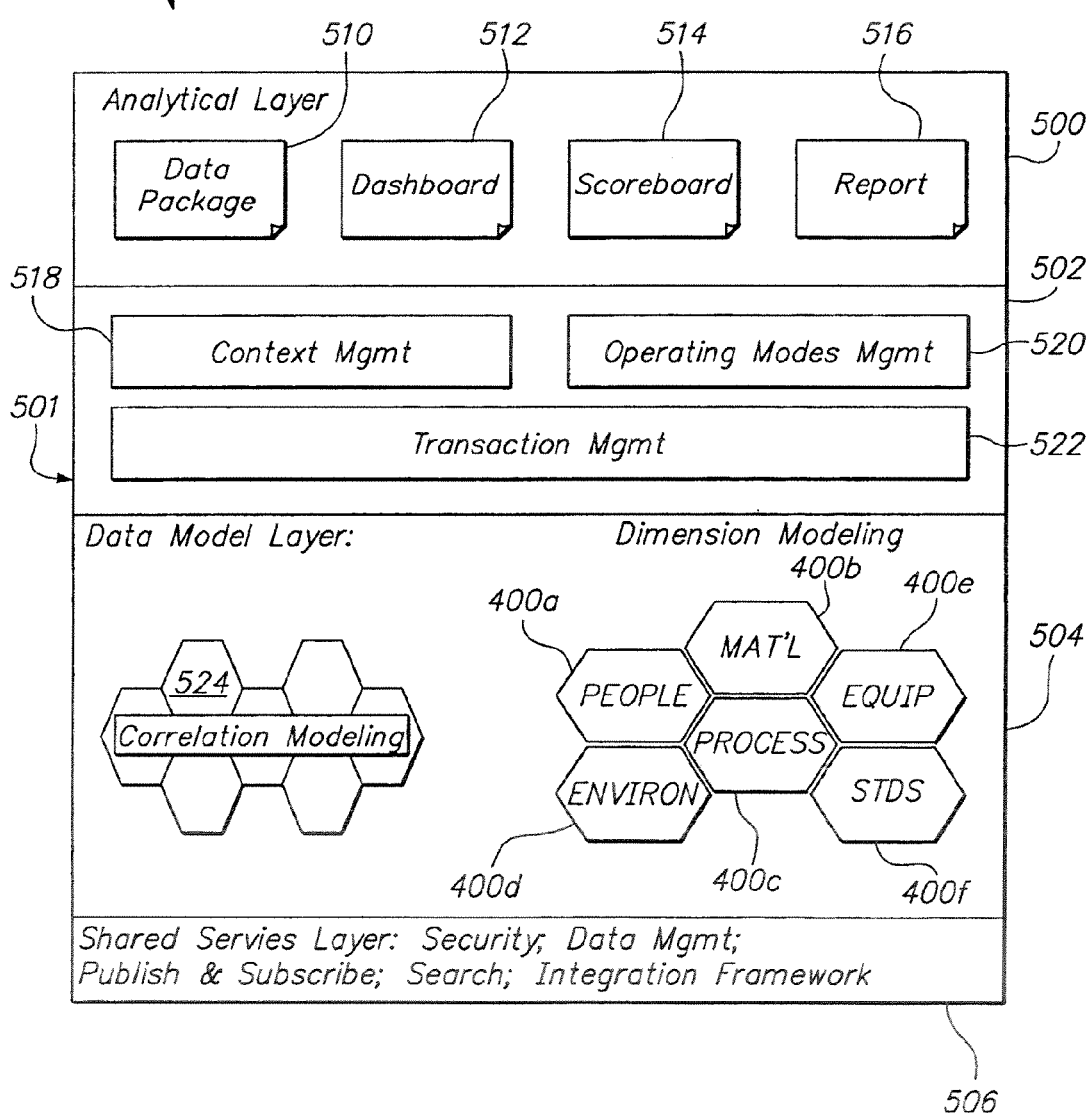
FIG. 5 illustrates a platform overview for the core module of the system.

Referring to FIG. 5, a platform overview 501 of the core module 1000 is shown. The platform overview 501 illustrates four layers of architecture for the core module 1000. Specifically, the core module 1000 has an analytical layer 500, a transaction layer 502, a data modeling layer 504 and a shared services layer 506. The core module 1000 establishes an enterprise wide platform that provides services, functions, and data models to create a base for product records. The architecture leverages J2EE technology for open-standard, multi-tiered enterprise architecture. Furthermore, the architecture provides published interfaces for development of applications and ensures interoperability through open interfaces, web services and XML.

The analytical layer 500 includes data package 510, dashboard 512, scorecard 514, and reports 516. The analytical layer 500 provides pre-defined reports and data packages, as well a pre-configured scorecards. Furthermore, analytical layer 500 ensures dashboard visibility and role-based reports and indicators.

The transaction layer 502 has context management 518, operating modes management 520 and transaction management 522. The transaction layer 502 provides pre-defined business processes and form templates and implements best practices. Furthermore, the transaction layer 502 provides a single user interface, lot traceability throughout production and in-progress visibility.

The data model layer 504 includes correlation modeling 524 and dimension modeling 400. The data model layer 504 only needs to be configured once and includes master libraries. The data model layer 504 is scalable and extendable and provides a central repository of related content. In this regard, the data model layer 504 is rapidly deployed and promotes reuse.

The shared services layer 506 provides security, data management, publish and subscribe services, search services and framework integration.

Figure 2:
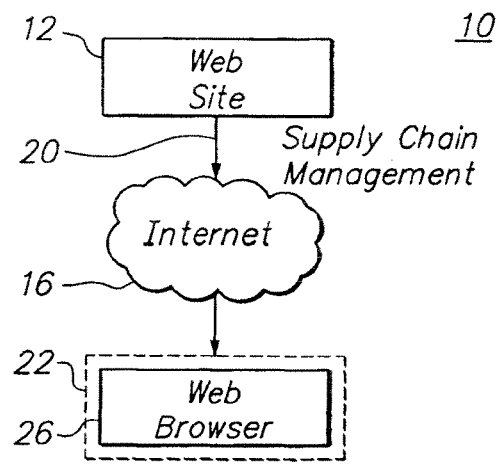
FIG. 2 is a diagram illustrating operation of an embodiment of a supply-side chain management application.

FIG. 2 is a diagram conceptually illustrating operation of an embodiment consistent with the present invention to provide infrastructure that will enable supply chain solutions for regulated industries. The supply chain solution 10 is used with a website 12, which represents one or more applications through which users can engage in worry-free management of their inventory, production, etc. A user with system 22 may interact with website 12 online (or otherwise) using a web browser 26 communicating through a network connection such as the Internet 16 or other type of network in order to obtain information about the status of their production for example.

Figure 3:
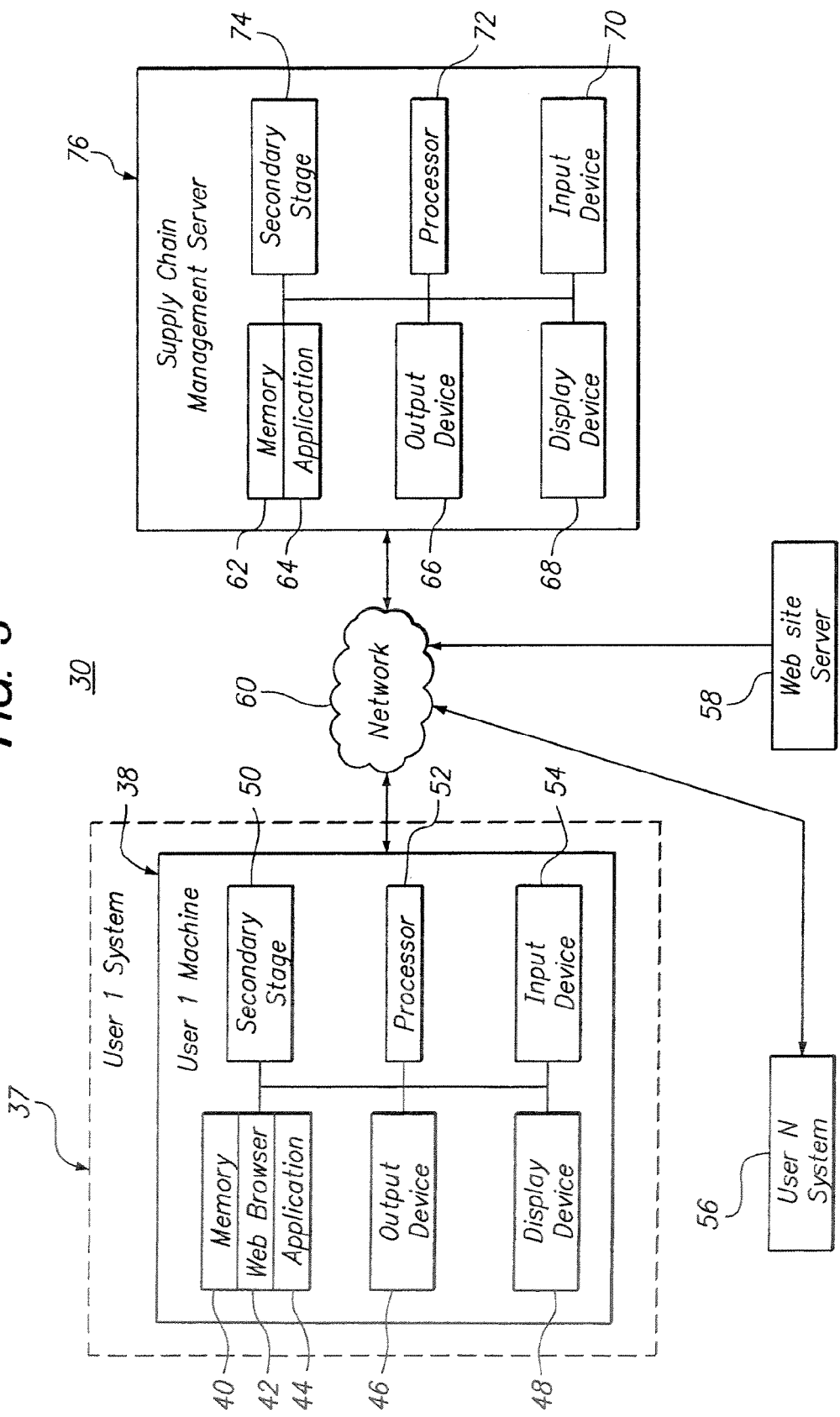
FIG. 3 is a block diagram illustrating hardware components for implementing a web based supply-side chain management application.

FIG. 3 is a block diagram illustrating exemplary hardware components for implementing system 10 for enabling supply chain solutions for regulated industries. System 30 includes a user system 37 having a user machine 38 connected with a network 60 such as the Internet, providing a network connection for participating in IP ordering. Other user systems, such as user system 56 may also be connected with network 60 for obtaining production status. User system 56, and other user systems, may include the same components as user system 37.

Users at user systems 37 and 56 interact with a server 76 to obtain production status information. Server 76 provides and maintains the web site 12 for providing a network connection to the application(s) through which users can obtain and share information. System 30 may also include the ability to access one or more web site servers 58 in order to obtain content from the World Wide Web, if desired. Only two user systems are shown for illustrative purposes, however, system 30 may include many user machines and may be scalable to add or delete user machines to or from the network.

User machine 38 illustrates typical components of a user machine. User machine 38 typically includes a memory 40, a secondary storage device 50, a processor 52, an input device 54, a display device 48, and an output device 46. Memory 40 may include random access memory (RAM) or similar types of memory, and it may store one or more applications 44, and a web browser 42, for execution by processor 52. Secondary storage device 50 may include a hard disk drive, floppy disk drive, CD-ROM drive, or other types of non-volatile data storage. Processor 52 may execute applications or programs stored in memory 40 or secondary storage 50, or received from the Internet or other network 60.

Input device 54 may include any device for entering information into machine 38, such as a keyboard, mouse, cursor-control device, touch-screen, microphone, digital camera, video recorder or camcorder. Display device 48 may include any type of device for presenting visual information such as, for example, a computer monitor or flat-screen display. Output device 46 may include any type of device for presenting a hard copy of information, such as a printer, and other types of output devices include speakers or any device for providing information in audio form.

Web browser 42 is used to access the application(s) through the web site 12 and display various web pages through which the user can collaborate information, and examples of those web pages are described below. Examples of web browsers include the Netscape Navigator program and the Microsoft Internet Explorer program. Any web browser, co-browser, or other application capable of retrieving content from a network and displaying pages or screens may be used.

Examples of user machines for interacting with the web site 12 include personal computers, laptop computers, notebook computers, palm top computers, network computers, or any processor-controlled device capable of executing a web browser or other type of application for interacting with the system.

Server 76 typically includes a memory 62, a secondary storage device 74, a processor 72, an input device 70, a display device 68, and an output device 66. Memory 62 may include RAM or similar types of memory, and it may store one or more applications 64 for execution by processor 72. Secondary storage device 74 may include a hard disk drive, floppy disk drive, CD-ROM drive, or other types of non-volatile data storage. Processor 72 executes the application(s), which is stored in memory 62 or secondary storage 74, or received from the Internet or other network 60. Input device 70 may include any device for entering information into server 76, such as a keyboard, mouse, cursor-control device, touch-screen, microphone, digital camera, video recorder or camcorder. Display device 68 may include any type of device for presenting visual information such as, for example, a computer monitor or flat-screen display. Output device 66 may include any type of device for presenting a hard copy of information, such as a printer, and other types of output devices include speakers or any device for providing information in audio form.

Also, processor 72 may execute one or more software applications 64 in order to provide the functions described in this specification, and the processing may be implemented in software, such as software modules, for execution by computers or other machines. The processing may provide and support web pages described in this specification and otherwise for display on display devices associated with the users' computers. The term "screen" refers to any visual element or combinations of visual elements for displaying information or forms; examples include, but are not limited to, user interfaces on a display device or information displayed in web pages or in windows on a display device. The screens may be formatted, for example, as web pages in Hypertext Markup Language (HTML), Extensible Markup Language (XML) or in any other suitable form for presentation on a display device depending upon applications used by users to interact with the system.

The screens include various sections, as explained below, to provide information or to receive information or commands. The term "section with respect to screens refers to a particular portion of a screen, possibly including the entire screen. Sections are selected, for example, to enter information or commands or to retrieve information or access other screens. The selection may occur, for example, by using a cursor-control device to "click on" or "double click on" the section. Alternatively, sections may be selected by entering a series of keystrokes or in other ways such as through voice commands or use of a touch screen. In addition, although the screens described below illustrate a particular arrangement and number of sections in each screen, other arrangements are possible and different numbers of sections in the screens may be used to accomplish the same or similar functions of displaying information and receiving information or commands. Also, the same section may be used for performing a number of functions, such as both displaying information and receiving a command.

Although only one server is shown, system 30 may use multiple servers as 15 necessary or desired to support the users and may also use back-up or redundant servers to prevent network downtime in the event of a failure of a particular server. In addition, although machine 37 and server 76 are depicted with various components, one skilled in the art will appreciate that these machines and the server can contain additional or different components. In addition, although aspects of an implementation consistent with the present invention are described as being stored in memory, one skilled in the art will appreciate that these aspects can also be stored on or read from other types of computer program products or computer-readable media, such as secondary storage devices, including hard disks, floppy disks, or CD-ROM; a carrier wave from the Internet or other network; or other forms of RAM or ROM. The computer-readable media may include instructions for controlling a computer system, such as machine 37 and server 76, to perform a particular method.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

The invention claimed is:

1. A method for managing the development and manufacturing of a beverage, the method comprising the steps of:
   recording information about the beverage during the development or manufacturing of the beverage in a single data layer using an operating mode selected from a plurality of operating modes, wherein each operating mode hi the plurality of operating modes affects a state that the information passes through and rules for verifying the information;
   assigning the information to a data dimension in a plurality of data dimensions, wherein the plurality of data dimensions comprises (i) a material dimension that stores material types, material attributes, and/or material hierarchy of materials used in the development or manufacturing of said beverage, (ii) a people dimension that stores an identity and role of people that participate in the development or manufacturing of said beverage, (iii) a standards dimension that stores internal standards for developing or manufacturing of the beverage or stores government imposed standards for developing or manufacturing of the beverage, (iv) an equipment dimension that sets valid limits, valid values, equipment characteristics, usage, and/or availability of equipment used in the development or manufacturing of the beverage, (v) an environment/facility dimension that tracks the facilities where processes used in the development or manufacturing of the beverage take place and the attributes of such facilities and, (vi) a process dimension that classifies the types of processes used in the development or manufacturing of the beverage, the workflow associated with each of the processes used in the development or manufacturing of the beverage, and the hierarchy of processes used in the development or manufacturing of the beverage, wherein the processes stored in the process dimension comprises a blend, a formulation, or a recipe;
   determining a plurality of permanent correlations between data dimensions in the plurality of data dimensions wherein the plurality of permanent correlations include a permanent correlation between a first data dimension and a second data dimension that are each independently selected from the group consisting of (i) said material dimension, (ii) said people dimension, (iii) said standards dimension, (iv) said equipment dimension, (v) said environment/facility dimension, and (vi) said process dimension, and wherein the plurality of permanent correlations span time and events in the development or manufacturing of the beverage thereby establishing compliance with regulatory standards;
   storing the plurality of permanent correlations in the single data layer;
   determining a context of the information;
   searching the permanent correlations of between the data dimensions in the plurality of data dimensions in response to the context;
   retrieving information from the plurality of dimensions and the plurality of permanent correlations about the development process or manufacturing of the beverage in view of the context;
   using said information to generate an electronic product history record or electronic development record for inclusion in a submission to a regulatory agency involved in the regulation of the development or manufacture of beverages; and
   including said electronic product history record or said electronic development record in said submission to said regulatory agency.

2. The method of claim 1 wherein the context defines changes to the information over time and events.

3. The method of claim 1, wherein the material dimension further comprises a chain of custody for the beverage, wherein the chain of custody includes a starting material for the beverage, a starting reagent for the beverage, a solvent used in the development of the beverage, or an intermediate of the beverage.

4. The method of claim 1, wherein the material dimension further comprises a chain of custody for the beverage, wherein the chain of custody includes a starting material for the beverage, a starting reagent for the beverage, a solvent used in the development of the beverage, and an intermediate of the beverage.

5. The method of claim 1, wherein the material dimension further comprises traceability of materials used to make the beverage.

6. The method of claim 1, wherein the information comprises an indication of who participated in the development or manufacture of the beverage, an indication of what people that participated in the development or manufacture of the beverage did in the development or manufacture of the beverage, an indication of where events leading to the development or manufacture of the beverage occurred, an indication of when events leading to the development or manufacture of the beverage transpired, and an indication of how events leading to the development or manufacture of the beverage occurred.

7. The method of claim 1, wherein the information comprises each request for a composition used in the development or manufacture of the beverage, each order for a composition used in the development or manufacture of the beverage, an inventory of each composition used in the development or manufacture of the beverage, each dispensal of each material used in the development or manufacture of the beverage, each disposal of each material used in the development or manufacture of the beverage, and each transfer of each material used in the development or manufacture of the beverage.

8. The method of claim 1 wherein the material dimension comprises a chain of documentation that includes material status, material signoff, material alert, material authentication, material electronic approval, or material hazard profile for materials used in the development or manufacture of the beverage.

9. The method of claim 1 wherein the material dimension comprises a chain of documentation that includes material status, material signoff, material alert, material authentication, material electronic approval, and material hazard profile for materials used in the development or manufacture of the beverage.

10. The method of claim 1, wherein the material dimension comprises quality of the beverage as determined by a material qualification identification, a use test, and the specifications of each raw material used in the development or manufacture of the beverage.

11. The method of claim 1, the method further comprising sorting each material used in the development or manufacture of the beverage based upon a material characteristic.

12. The method of claim 11, wherein the material characteristic is an evaluation date or a purity of the material.

13. The method of claim 1, wherein the equipment dimension comprises—a recordation of equipment used in the development or manufacture of the beverage, an identity of equipment used in the development or manufacture of the beverage, a characteristic of equipment used in the development or manufacture of the beverage, a recordation of equipment borrowed in the development or manufacture of the beverage, a record of equipment decommissioned in the development or manufacture of the beverage, or a maintenance record or cleaning record for equipment used in the development or manufacture of the beverage.

14. The method of claim 1, wherein the equipment dimension comprises a recordation of equipment used in the development or manufacture of the beverage, an identity of equipment used in the development or manufacture of the beverage, a characteristic of equipment used in the development or manufacture of the beverage, a recordation of equipment borrowed in the development or manufacture of the beverage, a record of equipment decommissioned in the development or manufacture of the beverage, and a maintenance record or cleaning record for equipment used in the development or manufacture of the beverage.

15. The method of claim 1, wherein the material dimension comprises a recordation of movement of raw and starting materials used during the development or manufacture of the beverage when the raw and starting materials are moved through the manufacturing process.

16. The method of claim 1, wherein the method further comprises:
  instructions for setting an inventory threshold level for each composition used in the development or manufacture of the beverage; and
  instructions for triggering a notification for a material when the inventory for the material drops below the inventory threshold level.

17. The method of claim 1, wherein the material dimension comprises an indication of material receipt, an indication of material issue, an indication or material return, an indication of material movement, or a verification of material movement, wherein the material is a raw material, an intermediate material, a bulk material, or a final product of the development or manufacture of the beverage.

18. The method of claim 1, wherein the single data layer is a single database or a single data structure.

19. The method of claim 1, wherein the people dimension sets default limits and valid values.

20. The method of claim 1, wherein a dimension in the plurality of dimensions stores a type, an attribute, and a status of the information.

21. The method of claim 1, the method further comprising providing an alerts interface through which each alert associated with objects in the information can be reviewed by a user, wherein the user can acknowledge an alert.

22. The method of claim 1, wherein process dimension further comprises an activity record or a lab analysis record performed during a stage of pharmaceutical manufacture of the beverage.

23. The method of claim 1, wherein the process dimension comprises each process step in the development or manufacture of the beverage, wherein, for each process step, the information comprises an identification of the people involved in the process step, an identification of the equipment used in the process step, an identification of the materials used in the process step, an identification of the standards followed in the process step, a description of the lab conditions of the lab used for the process step, or an identification of the facility location used for the process step.

24. The method of claim 1, wherein the process dimension comprises each process step in the development or manufacture of the beverage, wherein, for each process step, the information comprises an identification of the people involved in the process step, an identification of the equipment used in the process step, an identification of the materials used in the process step, an identification of the standards followed in the process step, a description of the lab conditions of the lab used for the process step, and an identification of the facility location used for the process step.

25. The method of claim 1, wherein the beverage is a pharmaceutical, a biopharmaceutical, or a generic compound.

26. The method of claim 1, wherein the material dimension comprises a certificate of analysis of a compound used in the development or manufacture of the beverage.

27. The method of claim 1, the method further comprising recording an audit trail of changes made to the information recorded in the single data layer.

28. The method of claim 1, wherein the information comprises a plurality of objects, wherein an object in the plurality of objects is a work order, a material receipt, or an equipment schedule, the method further comprising:
  assigning an alert that is triggered by a change in an attribute of an object in the plurality of objects in the single data layer.

29. The method of claim 28 wherein the change in the attribute is determined by an equality to a reference value, an inequality to a reference value, an increase over a reference value, a decrease below a reference value, a change into a range of values, or a change out of a range of values.

30. The method of claim 28 wherein the change in the attribute is a user action.

31. The method of claim 30 wherein the user action is user creation of an object, user modification of an object, or user deletion of an object.

32. The method of claim 28, wherein the method further comprises publishing the alert to a user that has subscribed to the alert.

33. The method of claim 32, wherein the alert is published to the user by e-mail, pager, or cell phone.

34. The method of claim 1, wherein the information comprises a plurality of objects, wherein an object in the plurality of objects is a work order, a material receipt, or an equipment schedule, the method further comprising assigning an alert that is triggered by a period of time.

35. The method of claim 1, the method further comprising providing an alerts interface through which each alert associated with objects in the information can be reviewed by a user, wherein the user can acknowledge an alert.

* * * * *

UNITED STATES PATENT AND TRADEMARK OFFICE
CERTIFICATE OF CORRECTION

PATENT NO.        : 7,797,327 B2  
APPLICATION NO.   : 11/859725  
DATED             : September 14, 2010  
INVENTOR(S)       : Anjali R. Kataria et al.

Page 1 of 1

It is certified that error appears in the above-identified patent and that said Letters Patent is hereby corrected as shown below:

In column 9, line 5, after "mechanism" insert -- . --.

In column 17, line 48, in claim 1, delete "hi" and insert -- in --, therefor.

In column 19, line 37, in claim 13, delete "comprises-a" and insert -- comprises a --, therefor.

Signed and Sealed this  
Sixteenth Day of August, 2011

David J. Kappos  
*Director of the United States Patent and Trademark Office*